United States Patent [19]

Soma et al.

[11] 4,219,465
[45] Aug. 26, 1980

[54] PIPERIDINE-SPIRO-HYDANTOIN DERIVATIVES AND THEIR USE AS POLYMER STABILIZERS

[75] Inventors: Nobuo Soma; Syoji Morimura; Takao Yoshioka; Tomoyuki Kurumada, all of Hiromachi, Japan

[73] Assignee: Sankyo Company Limited, Tokyo, Japan

[21] Appl. No.: 45,844

[22] Filed: Jun. 5, 1979

[30] Foreign Application Priority Data

Jun. 24, 1978 [JP] Japan .................................. 53-76694

[51] Int. Cl.$^2$ ....................... C07D 471/10; C08K 5/34
[52] U.S. Cl. ....................... 260/45.8 NT; 260/45.8 N; 260/45.85 B; 544/207; 546/20
[58] Field of Search ................ 260/45.8 NT; 544/209, 544/207; 546/20

[56] References Cited

U.S. PATENT DOCUMENTS

| | | | |
|---|---|---|---|
| 3,925,376 | 12/1975 | Chalmers et al. | 544/209 |
| 3,975,462 | 8/1976 | Murayama et al. | 260/45.8 NT |
| 4,086,204 | 4/1978 | Cassandrini et al. | 544/209 |
| 4,097,587 | 6/1978 | Soma et al. | 546/20 |
| 4,108,829 | 8/1978 | Cassandrini et al. | 544/209 |
| 4,162,246 | 7/1979 | Soma et al. | 546/20 |

*Primary Examiner*—Hosea E. Taylor
*Assistant Examiner*—R. A. White
*Attorney, Agent, or Firm*—Toren, McGeady and Stanger

[57] ABSTRACT

Novel piperidine-spiro-hydantoin derivatives represented by the general formula (I) and use thereof as light stabilizers for synthetic polymers are described:

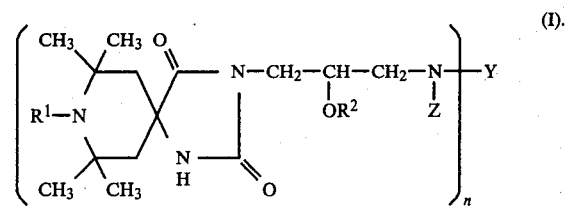

The compounds are distinguished by an improved stabilizing effect in various synthetic polymer compositions, such as polyolefins, against light- and/or heat-induced deterioration thereof, small volatility upon heat-processing or during storage of shaped articles containing the compounds, and resistance to extraction with water and solvents.

11 Claims, No Drawings

PIPERIDINE-SPIRO-HYDANTOIN DERIVATIVES AND THEIR USE AS POLYMER STABILIZERS

The present invention relates to a novel piperidinespiro-hydantoin derivative, an acid addition salt thereof, and their use as a stabilizer for synthetic polymers.

A certain kind of the piperidine-spiro-hydantoin derivative has been disclosed as a stabilizer for synthetic polymers, for example, in U.S. Pat. Nos. 3,542,729, 3,639,409, 3,705,126, 3,898,303, 3,941,744, 3,975,462 and 4,097,587; and Japanese Patent Provisional Publications No. 49-72332.

However, there has not been known the compound in which 2-hydroxy-3-(7,7,9,9-tetramethyl-2,4-dioxo-1,3,8-triazaspiro[4.5]dec-3-yl)propyl group, for example, is directly combined with the nitrogen atom of amine derivative. The present inventors have discovered that such compounds as well as their acid addition salts are a stabilizer exhibiting an outstanding effect toward the light- and heat-induced deterioration of synthetic polymers, and further possessing a low heat-volatility and a low migration property.

The novel piperidine-spiro-hydantoin derivative of the present invention may be represented by the following formula (I)

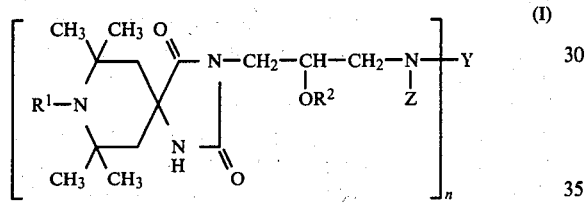

and an acid addition salt thereof, wherein,
$R^1$ represents hydrogen or methyl,
$R^2$ represents hydrogen or an acyl group having not more than 18 C-atoms,
n is 1 or 2,
when n is 1,
Y and Z may be the same or different and represent hydrogen, an alkyl group having from 1–18 C-atoms, an alkenyl group having from 3–18 C-atoms, a cycloalkyl group having from 5–7 C-atoms, a phenyl group optionally substituted with methyl, an aralkyl group having 7 or 8 carbon atoms, a group of the formula

(wherein $R^3$ represents hydrogen or methyl and $R^4$ represents hydrogen or an acyl group having not more than 18 carbon atoms;) 2,2,6,6-tetramethyl-4-piperidyl or 1,2,2,6,6-pentamethyl-4-piperidyl or a group of the formula

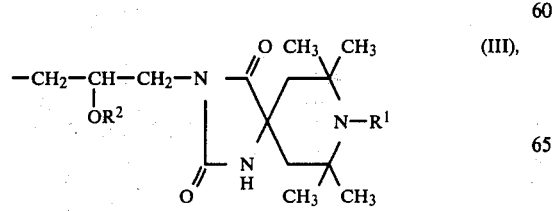

or Y and Z may be joined together to form a tetramethylene, pentamethylene, 3-oxapentamethylene, succinyl, glutaryl, maleoyl or phthaloyl group or a group of the formula

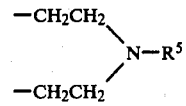

wherein $R^5$ is a group of the formula (III), with the proviso that $R^2$ and $R^4$ are hydrogen when Y and/or Z are hydrogen and that $R^2$ and $R^4$ are each hydrogen or an acyl group as defined or $R^2$ is hydrogen and $R^4$ is an acyl group as defined when Y and Z are both a group of formula (II) or one of Y and Z is a group of the formula (II) and the other is different from hydrogen;
when n is 2,
Y represents an alkylene group having from 2–6 carbon atoms, a phenylene group which may be substituted by methyl, p-xylylene, 1,4-cyclohexylene, the 4,4'-diphenylether or 4,4'-diphenylmethane radical, 2,4-s-triazinediyl, 6-methyl- or 6-phenyl-2,4-s-triazinediyl, and
Z represents a group of the formula (III), 2,2,6,6-tetramethyl-4-piperidyl or 1,2,2,6,6-pentamethyl-4-piperidyl. In the formula (I),
when n is 1 and
Y and Z represent an alkyl group having from 1 to 18 carbon atoms, they may be, for example, methyl, ethyl, n-propyl, i-propyl, n-butyl, i-butyl, t-butyl, 2-ethyl-hexyl, octyl, 2,2,4,4-tetramethylpentyl, decyl, dodecyl, tetradecyl, hexadecyl or octadecyl group, preferably an alkyl group having from 4 to 18 carbon atoms and most preferably an alkyl group having from 8 to 18 carbon atoms;
Y and Z represent an alkenyl group having from 3 to 18 carbon atoms, they may be, for example, allyl, propenyl, 2-butenyl, 2-pentenyl, 2-hexenyl, 2-octenyl, 5-decenyl, 6-dodecenyl, 7-tetradecenyl, 8-hexadecenyl, or 9-octadecenyl group, preferably allyl or 9-octadecenyl group;
Y and Z represent a cycloalkyl group having from 5 to 7 carbon atoms, they are cyclopentyl, cyclohexyl or cycloheptyl, preferably cyclohexyl group;
Y and Z represent a phenyl group which may be optionally substituted with methyl group, they are phenyl or o-, m- or p-tolyl group; and
Y and Z represent an aralkyl group having 7 or 8 carbon atoms, they may be, for example, benzyl or phenethyl group, preferably benzyl group.
When n is 2 and
Y represents an alkylene group having from 2 to 6 carbon atoms, it may be, for example, ethylene, trimethylene or hexamethylene group;
Y represents a phenylene group which may be optionally substituted with methyl group, it may be, for example, 1,2-phenylene, 1,3-phenylene, 1,4-phenylene, 2,3-tolylene, 2,4-tolylene or 2,5-tolylene group; and
represents 2,4-s-triazinediyl, 6-methyl- or 6-phenyl-2,4-s-triazinediyl group, preferably 6-phenyl-2,4-s-triazinediyl.
When $R^2$ and/or $R^4$ represent an acyl group having not more than 18 carbon atoms, they may be, for example, an aliphatic, aromatic, araliphatic or alicyclic acyl group (the aromatic moiety of the said acyl group may be optionally substituted with alkyl group having from 1 to 4 carbon atoms and/or hydroxy group), preferably a group of the formula —$COR^6$ ($R^6$ in the formula may be an alkyl group having from 1 to 17 carbon atoms; an alkenyl group having 2 or 3 carbon atoms; a phenyl, benzyl or phenethyl group in which the phenyl moiety may be optionally substituted either with one $C_{1-4}$ alkyl group or with two $C_{1-4}$ alkyl groups and one hydroxy group; styryl group; or cyclohexyl group) such as, for example, acetyl, propionyl, valeryl, octanoyl, 2-ethylhexanoyl, lauroyl, palmitoyl, stearoyl, acryloyl, crotonoyl, methacryloyl, benzoyl, o-, m- or p-toluoyl, p-tert-butylbenzoyl, 3,5-di-tert-butyl-4-hydroxybenzoyl, phenylacetyl, 3,5-di-tert-butyl-4-hydroxyphenylacetyl, 3-(3,5-di-tert-butyl-4-hydroxyphenyl)propionyl, cinnamoyl or cyclohexanecarbonyl group. The most preferable acyl group is an alkanoyl group having not more than 18 carbon atoms, 3-(3,5-di-tert-butyl-4-hydroxyphenyl)propionyl group, or a benzoyl group which may be optionally substituted with alkyl group having from 1 to 4 carbon atoms.

The compound in which $R^2$ and $R^4$ are hydrogen atoms may also be preferable.

The preferable compounds of the formula (I) of the present invention may be those in which (1) n represents 1 or 2,
  when n is 1,
    Y and Z represent hydrogen atom, an alkyl group having from 1–18 carbon atoms, an alkenyl group having from 3–18 carbon atoms, a cycloalkyl group having from 5–7 carbon atoms, an aralkyl group having 7 or 8 carbon atoms, a group of the formula (II) or a group of the formula (III) with the proviso that, when Y and Z both represent alkyl, alkenyl, cycloalkyl, aralkyl or a group of the formula (II) as defined, said groups are identical, and when n is 2,
    Y represents an alkylene group having from 2–6 carbon atoms, p-xylylene, 2,4-s-triazinediyl, 6-methyl- or 6-phenyl-2,4-s-triazinediyl, and Z represents a group of the formula (III).

Particularly preferable compounds in (1) are those in which $R^2$ represents hydrogen atom.

More preferable compounds of the formula (I) may be those in which (2) n is 1,
    $R^2$ represents hydrogen atom,
    Y represents an alkyl group having from 1–18 carbon atoms, a cycloalkyl or benzyl group, and
    Z represents hydrogen atom or a group of the formula (III).

(3) n is 2,
    Z represents a group of the formula (III),
    $R^2$ represents hydrogen atom, and
    Y represents an alkylene group having from 2–6 carbon atoms, p-xylylene group or 6-phenyl-2,4-s-triazinediyl group.

The most preferable compounds of the formula (I) may be those in which (4) n is 1,
    Z represents a group of the formula (III),
    $R^2$ represents hydrogen atom, and
    Y represents an alkyl group having from 1–18 carbon atoms, cyclohexyl group or benzyl group, particularly an alkyl group having from 8–18 carbon atoms.

And further, the following compounds may be also preferable in which (5)
    $R^2$ represents hydrogen atom,
    Z represents 2,2,6,6-tetramethyl-4-piperidyl or 1,2,2,6,6-pentamethyl-4-piperidyl group,
n represents 1 or 2,
    when n is 1,
        Y represents an alkyl group having from 1–18 carbon atoms, and
    when n is 2,
        Y represents an alkylene group having from 2–6 carbon atoms, and (6) when Y and/or Z represent a group of the formula (III) or a group of the formula (II),
    $R^2$ and/or $R^4$ represent an alkanoyl group having not more than 18 carbon atoms, 3-(3,5-di-tert-butyl-4-hydroxyphenyl)propionyl group, or a benzoyl group which may be optionally substituted with alkyl group having from 1–4 carbon atoms.

The acid addition salt of the compound of the formula (I) is also included in the scope of the present invention. As to the acid addition salt there is no particular limitation so far as it does not affect on the stability of polymers, and the acid employable may be, for example, an inorganic acid such as sulfuric acid, hydrochloric acid or phosphoric acid; an organic carboxylic acid such as formic acid, acetic acid, valeric acid, stearic acid, oxalic acid, adipic acid, sebacic acid, maleic acid, benzoic acid, p-tert-butylbenzoic acid, 3,5-di-tert-butyl-4-hydroxybenzoic acid, salicylic acid or terephthalic acid; an organic sulfonic acid such as methanesulfonic acid or p-toluenesulfonic acid; or an organic phosphonic acid such as phenylphosphonic acid.

Below are listed individual piperidine-spiro-hydantoin derivative of the formula (I) without an limitation thereby. The number given to the compounds will be employed in Example for indicating these compounds.
When n is 1
  (a) the compound in which Z is hydrogen atom

| Compound No. | $R^1$ | $R^2$ | Y |
|---|---|---|---|
| a - 1 | H | H | H |
| 2 | $CH_3$ | H | H |
| 3 | H | H | n-$C_3H_7$— |
| 4 | $CH_3$ | H | $1$-$C_3H_7$— |
| 5 | $CH_3$ | H | n-$C_4H_9$— |
| 6 | $CH_3$ | H | t-$C_4H_9$— |
| 7 | $CH_3$ | H | $CH_3(CH_2)_3CHCH_2$—<br>$\mid$<br>$C_2H_5$ |
| 8 | $CH_3$ | H | n-$C_8H_{17}$— |
| 9 | H | H | n-$C_{10}H_{21}$— |
| 10 | $CH_3$ | H | n-$C_{10}H_{21}$— |
| 11 | H | H | n-$C_{12}H_{25}$— |
| 12 | $CH_3$ | H | n-$C_{12}H_{25}$— |
| 13 | $CH_3$ | H | n-$C_{14}H_{29}$— |
| 14 | H | H | n-$C_{16}H_{33}$— |
| 15 | $CH_3$ | H | n-$C_{16}H_{33}$— |
| 16 | H | H | n-$C_{18}H_{37}$— |
| 17 | $CH_3$ | H | n-$C_{18}H_{37}$— |
| 18 | $CH_3$ | H | $CH_2$=$CH$—$CH_2$— |
| 19 | H | H | $CH_3(CH_2)_7CH$=$CH(CH_2)_8$— |
| 20 | H | H | 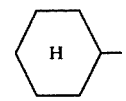 |

-continued

| Compound No. | R¹ | R² | Y |
|---|---|---|---|
| 21 | CH₃ | H | cyclohexyl |
| 22 | CH₃ | H | phenyl |
| 23 | H | H | 3-methylphenyl |
| 24 | H | H | benzyl (–CH₂–C₆H₅) |

-continued

| Compound No. | R¹ | R² | Y |
|---|---|---|---|
| 25 | CH₃ | H | –CH₂–C₆H₅ |
| 26 | H | H | HOCH₂CH₂– |
| 27 | CH₃ | H | HOCH₂CH₂– |
| 28 | H | H | HOCH(CH₃)–CH₂– |
| 29 | CH₃ | H | HOCH(CH₃)–CH₂– |
| 29 | CH₃ | H | 2,2,6,6-tetramethylpiperidin-4-yl (HN ring) |

(b) the compound in which Z is the group of the formula (III)

| Compound No. | R¹ | R² | Y |
|---|---|---|---|
| b-1 | H | H | H |
| 2 | CH₃ | H | H |
| 3 | H | H | CH₃– |
| 4 | CH₃ | H | n-C₃H₇– |
| 5 | CH₃ | H | i-C₃H₇– |
| 6 | H | H | n-C₄H₉– |
| 7 | CH₃ | H | n-C₄H₉– |
| 8 | H | H | CH₃(CH₂)₃CH(C₂H₅)CH₂– |
| 9 | CH₃ | H | n-C₈H₁₇– |
| 10 | H | H | n-C₁₀H₂₁– |
| 11 | CH₃ | H | n-C₁₀H₂₁– |
| 12 | H | H | n-C₁₂H₂₅– |
| 13 | CH₃ | H | n-C₁₂H₂₅– |
| 14 | H | (C₆H₅–CO–) | n-C₁₂H₂₅– |
| 15 | H | H | n-C₁₄H₂₉– |
| 16 | CH₃ | H | n-C₁₄H₂₉– |
| 17 | H | H | n-C₁₆H₃₃– |
| 18 | CH₃ | H | n-C₁₆H₃₃– |
| 19 | H | H | n-C₁₈H₃₇– |
| 20 | CH₃ | H | n-C₁₈H₃₇– |
| 21 | CH₃ | CH₃CO– | n-C₁₈H₃₇– |
| 22 | CH₃ | H | CH₂=CH–CH₂– |
| 23 | H | H | CH₃(CH₂)₇CH=CH(CH₂)₈– |
| 24 | H | H | cyclopentyl |
| 25 | H | H | cyclohexyl |
| 26 | CH₃ | H | cyclohexyl |
| 27 | H | H | phenyl |

-continued

| Compound No. | R¹ | R² | Y |
|---|---|---|---|
| 28 | CH₃ | H | 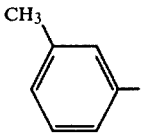 3-methylphenyl |
| 29 | H | H | 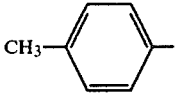 4-methylphenyl |
| 30 | H | H | 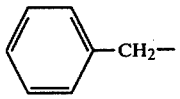 benzyl (-CH₂-) |
| 31 | CH₃ | H | 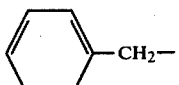 benzyl (-CH₂-) |
| 32 | H | H | HOCH₂CH₂— |
| 33 | CH₃ | H | HOCH₂CH₂— |
| 34 | H | n-C₄H₉CO— | n-C₄H₉COOCH₂CH₂— |
| 35 | CH₃ | n-C₁₁H₂₃CO— | n-C₁₁H₂₃COOCH₂CH₂— |
| 36 | CH₃ | H | HOCHCH₂—<br>    |<br>    CH₃ |
| 37 | CH₃ | 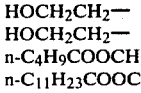 HO—⬡—CH₂CH₂CO— | 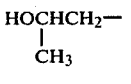 HO—⬡—CH₂CH₂COOCH₂CH₂— |
| 38 | H | H | 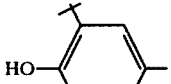 tetramethylpiperidinyl (NH) |

(c) the compound in which Z is the same group as Y

| Compound No. | R¹ | R² | Z,Y |
|---|---|---|---|
| c-1 | CH₃ | H | C₂H₅— |
| 2 | CH₃ | CH₃CO— | i-C₃H₇— |
| 3 | H | H | n-C₈H₁₇— |
| 4 | CH₃ | H | n-C₁₀H₂₁— |
| 5 | H | H | n-C₁₂H₂₅— |
| 6 | CH₃ | H | CH₃(CH₂)₇CH=CH(CH₂)₈— |
| 7 | CH₃ | H | 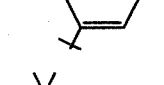 cyclohexyl |
| 8 | H | H | 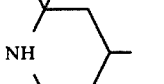 phenyl |
| 9 | CH₃ | H | 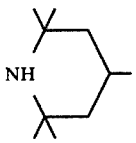 benzyl (-CH₂-) |
| 10 | H | H | HOCH₂CH₂— |
| 11 | CH₃ | H | HOCH₂CH₂— |
| 12 | CH₃ | H | n-C₄H₉COOCH₂CH₂— |
| 13 | CH₃ | n-C₁₁H₂₃CO— | n-C₁₁H₂₃COOCH₂CH₂— |
| 14 | CH₃ | H | n-C₁₇H₃₅COOCH₂CH₂— |

-continued

| Compound No. | R¹ | R² | Z,Y |
|---|---|---|---|
| 15 | CH₃ | C₆H₅—CO— | C₆H₅—COOCH₂CH₂— |
| 16 | CH₃ | (t-Bu substituted)C₆H₃—CO— | (t-Bu substituted)C₆H₃—COOCH₂CH₂— |
| 17 | CH₃ | H | HO—(di-t-Bu)C₆H₂—CH₂CH₂COOCH₂CH₂— |
| 18 | CH₃ | HO—(di-t-Bu)C₆H₂—CH₂CH₂CO— | HO—(di-t-Bu)C₆H₂—CH₂CH₂COOCH₂CH₂— |
| 19 | CH₃ | H | HO—CH(CH₃)—CH₂— |
| 20 | CH₃ | H | [N-acetamido-tetramethyl-N-methylpiperidinyl]—C(=O)—N—CH₂CH(OH)CH₂— |

(d) the compound in which Z and Y are a different group

| Compound No. | R¹ | R² | Y | Z |
|---|---|---|---|---|
| d-1 | CH₃ | H | C₂H₅— | n-C₄H₉— |
| 2 | CH₃ | H | CH₃— | C₆H₅— |
| 3 | H | H | CH₃— | C₆H₅—CH₂— |
| 4 | CH₃ | H | n-C₄H₉— | (tetramethylpiperidinyl, HN) |
| 5 | CH₃ | H | n-C₈H₁₇— | (N-methyl tetramethylpiperidinyl, CH₃—N) |
| 6 | H | H | n-C₁₂H₂₅— | (tetramethylpiperidinyl, HN) |
| 7 | H | H | C₆H₅—CH₂— | (tetramethylpiperidinyl, HN) |
| 8 | H | H | HOCH₂CH₂— | (tetramethylpiperidinyl, HN) |

(e) the compound in which Y and Z are joined together to form a group

| Compound No. | R¹ | R² | Y + Z |
|---|---|---|---|
| e-1 | CH₃ | H | —(CH₂)₅— |
| 2 | CH₃ | H | —(CH₂)₂—O—(CH₂)₂— |
| 3 | CH₃ | H | —CO—(CH₂)₂—CO— |

-continued

| Compound No. | R¹ | R² | Y + Z |
|---|---|---|---|
| 4 | H | H | —CO—⟨phenyl⟩—CO— |
| 5 | CH₃ | H | —CH₂CH₂\N—CH₂CHCH₂—N—CO—⟨tetramethylpiperidine-N—CH₃⟩ / —CH₂CH₂ ... OH ... NH—CO | when n is 2

(f) the compound in which Z is the group of the formula (III)

| Compound No. | R¹ | R² | Y |
|---|---|---|---|
| f-1 | H | H | —(CH₂)₂— |
| 2 | H | H | —(CH₂)₆— |
| 3 | CH₃ | H | —(CH₂)₆— |
| 4 | CH₃ | H | —⟨C₆H₄⟩— |
| 5 | H | H | —⟨C₆H₃(CH₃)⟩— |
| 6 | CH₃ | H | —CH₂—⟨C₆H₄⟩—CH₂— |
| 7 | CH₃ | H | —⟨cyclohexyl⟩— |
| 8 | CH₃ | H | —⟨C₆H₄⟩—O—⟨C₆H₄⟩— |
| 9 | CH₃ | H | —⟨C₆H₄⟩—CH₂—⟨C₆H₄⟩— |
| 10 | CH₃ | H | ⟨triazine with H⟩ |
| 11 | CH₃ | H | ⟨triazine with CH₃⟩ |
| 12 | H | H | ⟨triazine with phenyl⟩ |
| 13 | CH₃ | H | ⟨triazine with phenyl⟩ |
| 14 | CH₃ | CH₃CO— | ⟨triazine with phenyl⟩ |

(g) the compound in which Z is not a group of the formula (III)

| Compound No. | R¹ | R² | Y | Z |
|---|---|---|---|---|
| g-1 | H | H | —(CH₂)₂— | HN⟨piperidine⟩ |
| 2 | H | H | —(CH₂)₆— | HN⟨piperidine⟩ |
| 3 | CH₃ | H | —(CH₂)₆— | CH₃—N⟨piperidine⟩ |

The piperidine-spiro-hydantoin derivative of the formula (I) of the present invention may be prepared by reacting an amino derivative with a requisite amount of 3-(2,3-epoxypropyl)-piperidine-spiro-hydantoin derivative and, if desired, by acylating the product.

More particularly, the compound of the formula (I) may be prepared by reacting a compound of the formula $$\left[ \begin{array}{c} H-N-Y^1 \\ | \\ Z^1 \end{array} \right]_n \quad (IV)$$

[in the formula, n represents 1 or 2.
When n is 1,
$Y^1$ and $Z^1$ may be the same or different and represent hydrogen atom, a $C_{1-18}$ alkyl, a $C_{3-18}$ alkenyl, a $C_{5-7}$ cycloalkyl, a phenyl which may be optionally substituted with methyl group or a $C_{7-8}$ aralkyl group, a group of the formula $$-CH_2-CH-OH \atop |\atop R^3$$

($R^3$ has the same meaning as defined above), or 2,2,6,6-tetramethyl-4-piperidyl or 1,2,2,6,6-pentamethyl-4-piperidyl group. Or
$Y^1$ and $Z^1$ may jointly together represent tetramethylene, pentamethylene, 3-oxapentamethylene, succinyl, glutaryl, maleoyl or phthaloyl group, or $$\begin{array}{c} -CH_2CH_2 \\ \phantom{-CH_2CH_2}\diagdown \\ \phantom{-CH_2CH_2}\phantom{xx}NH. \\ \phantom{-CH_2CH_2}\diagup \\ -CH_2CH_2 \end{array}$$

When n is 2,
$Y^1$ represents a $C_{2-6}$ alkylene, a phenylene which may be optionally substituted with methyl group, p-xylylene group, 1,4-cyclohexylene group, 4,4'-diphenylether group, 4,4'-diphenylmethane group, 2,4-s-triazinediyl group, 6-methyl-2,4-s-triazinediyl group or 6-phenyl-2,4-triazinediyl group.
$Z^1$ represents hydrogen atom, 2,2,6,6-tetramethyl-4-piperidyl or 1,2,2,6,6-pentamethyl-4-piperidyl group.]
with an appropriate amount of a compound of the formula (V)

($R^1$ in the formula has the same meaning as defined above) to prepare a compound of the formula (VI)

[in the formula, n represents 1 or 2,
when n is 1, $Y^2$ and $Z^2$ may be the same or different and represent hydrogen atom, a $C_{1-18}$ alkyl, a $C_{3-18}$ alkenyl, a $C_{5-7}$ cycloalkyl, a phenyl which may be optionally substituted with methyl group or a $C_{7\,or\,8}$ aralkyl group, a group of the formula $$-CH_2-CH-OH \atop |\atop R^3$$

($R^3$ has the same meaning as defined above), 2,2,6,6-tetramethyl-4-piperidyl or 1,2,2,6,6-pentamethyl-4-piperidyl group or a group of the formula (III) in which $R^2$ is hydrogen atom. Or
$Y^2$ and $Z^2$ may jointly together represent tetramethylen, pentamethylene, 3-oxapentamethylene, succinyl, glutaryl, maleoyl or phthaloyl group, or a group of the formula $$\begin{array}{c} -CH_2CH_2 \\ \phantom{-CH_2CH_2}\diagdown \\ \phantom{-CH_2CH_2}\phantom{xx}N-R^{5'} \\ \phantom{-CH_2CH_2}\diagup \\ -CH_2CH_2 \end{array}$$

($R^{5'}$ represents a group of the formula (III) in which $R^2$ is hydrogen atom).
When n is 2,
$Y^2$ represents a $C_{2-6}$ alkylene, a phenylene which may be optionally substituted with methyl group, p-xylylene group, 1,4-cyclohexylene group, 4,4'-diphenylether group, 4,4'-diphenylmethane group, 2,4-s-triazinediyl group, 6-methyl-2,4-s-triazinediyl group or 6-phenyl-2,4-s-triazinediyl group
$Z^2$ represents 2,2,6,6-tetramethyl-4-piperidyl or 1,2,2,6,6-pentamethyl-4-piperidyl group or a group of the formula (III) in which $R^2$ is hydrogen atom] and, if desired, by acylating subsequently the product according to the usual manner.

In preparing the compound of the above-described formula (VI), the amount to be used of the compound of the above-described formula (V) is required suitably depending upon the number of the group of the formula (III) (wherein $R^2$ is hydrogen atom) to be introduced into the compound of the above-described formula (IV).

The reaction is carried out by heating a mixture of the amino derivative of the above-described formula (IV) and an appropriate amount of the compound of the above-described formula (V) at from room temperature to 200° C., preferably at from 50° to 150° C. in the presence or absence of inert organic solvent. As to the solvent there is no particular limitation so far as it is indifferent to the reaction, and there may be employed, for example, water; an ether such as dioxane, diethylene glycol, dimethyl ether or the like; a dialkyl amide such as dimethyl formamide, dimethyl acetamide or the like; an aliphatic hydrocarbon such as n-hexane, n-heptane or the like; a chlorinated or non-chlorinated aromatic hydrocarbon such as benzene, toluene, xylene, chlorobenzene, p-dichlorobenzene or the like; an alcohol such as anhydrous or hydrous methanol, ethanol, n- or t-butanol or the like; but preferably aromatic hydrocarbons and anhydrous or hydrous alcohols are used, and particularly preferable are anhydrous or hydrous alcohols. The reaction is favorably carried out in the presence of a basic alkali metal compound such as sodium hydroxide, potassium hydroxide, potassium carbonate or the like.

When the compound of the above-described formula (VI) is desired to be acylated, the reaction is carried out by reacting the compound of the above-described formula (VI) with a reactive derivative of the carboxylic acid (acid halide, acid anhydride or acid lower alkyl ester) corresponding to the acyl group to be introduced. The acylating agent may be suitably selected depending upon the sort of the acyl group to be introduced, but the use of an acid lower alkyl ester is particularly preferable. The amount of the acylating agent to be employed may be varied depending upon the number of the acyl group to be introduced.

In case of using an acid ester, the reaction is conveniently carried out in an inert organic solvent in the presence of a strong base. As preferable solvent there may be used, for example, an aromatic or aliphatic hydrocarbon such as benzene, toluene, xylene, n-heptane, n-octane, i-octane or the like. As suitable strong base there may be used, for example, a strongly basic alkali metal compound such as sodium methylate, sodium ethylate, potassium hydroxide, lithium amide or the like, or a titanic acid derivative such as tetraisopropyl titanate or tetrabutyl titanate. The reaction proceeds conveniently by heating usually at 80°–180° C.

When an acid halide is employed, the reaction is conveniently carried out in an inert organic solvent in the presence of an acid-binding agent. As the solvent there may be preferably used, for example, an aromatic hydrocarbon such as benzene, toluene, xylene or the like; a halogenated aliphatic hydrocarbon such as chloroform, trichloroethane or the like; or an ether such as diethyl ether, tetrahydrofuran, dioxane or the like. As the acid-binding agent there may be preferably used, for example, an alkali metal hydroxide such as sodium hydroxide, potassium hydroxide or the like; an alkali metal carbonate such as sodium carbonate, potassium carbonate or the like; or an organic base such as triethylamine, pyridine or the like. The reaction is usually carried out at 0°–130° C.

When an acid anhydride is employed, the reaction is carried out in the presence of an inert organic solvent or in the absence of an inert organic solvent using the excess of acid anhydride. As the solvent there may be preferably used, for example, an aromatic hydrocarbon such as benzene, toluene, xylene or the like; or an ether such as dioxane, tetrahydrofuran, diethylene glycol, dimethyl ether or the like. The reaction is usually carried out at from room temperature to 160° C.

The piperidine-spiro-hydantoin derivatives of the formula (I) and their acid addition salts according to the present invention exhibit a low heat-volatility as well as a low migration property, and they are effective for stabilizing the light- and heat-induced-deteriorations of a wide range of synthetic polymers. The following may be included as the polymers which can be stabilized by these compounds:

olefin and diene polymers
including homopolymers of olefins and dienes (e.g. low-density, high-density and cross-linked polyethylenes, polypropylene, polyisobutylene, polymethylbutene-1, polymethylpentene-1, polyisoprene and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymer, propylene/butene-1 copolymer, propylene/isobutene copolymer, ethylene/butene-1 copolymer, and terpolymers of ethylene and propylene with dienes such as hexadiene, dicyclopentadiene or ethylidene norbornene);

styrene polymers
including polystyrene, copolymers of styrene and of α-methylstyrene (e.g. styrene/butadiene copolymers, styrene/acrylonitrile copolymers, styrene/acrylonitrile/methyl methacrylate copolymers, styrene/acrylonitrile/acrylic ester copolymers, styrene/acrylonitrile copolymers modified with acrylic ester polymers to provide impact strength, and styrene polymers modified with EPDM to provide impact strength), and graft copolymers of styrene (e.g. polymers in which styrene is grafted onto polybutadiene, and polymers in which styrene and acrylonitrile are grafted onto polybutadiene usually called as acrylonitrile/butadiene/styrene or ABS plastics);

halogenated vinyl and vinylidene polymers
including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids
and derivatives thereof, including polyacrylates and polymethacrylates, polyacrylamides and polyacrylonitrile;

polymers derived from unsaturated alcohols and amines
and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers
including hompolymers and copolymers derived from epoxides (e.g. polyethylene oxide) and polymers derived from bisglycidyl ethers;

polyacetals, polyalkylene oxides and polyphenylene oxides
including polyoxymethylene, oxymethylene/ethylene oxide copolymers, polyoxyethylene, polypropylene oxide, polyisobutylene oxide and polyphenylene oxides;

polyurethanes and polyureas;

polycarbonates;

polysulfones;

polyamides and copolyamides
derived from diamines and aliphatic or aromatic dicarboxylic acids and/or from aminocarboxylic acids or the corresponding lactams, including nylon-6, nylon-6/6, nylon-6/10, nylon-11 and nylon-12;

polyesters
derived from dicarboxylic acid and dialcohols and/or from hydroxycarboxylic acids and the corresponding lactones, including polyethylene glycol terephthalate and poly-1,4-dimethylol-cyclohexane terephthalate;

cross-linked polymers derived from aldehydes together with phenols, ureas, or melamines, e.g. phenol/formaldehyde, urea/formaldehyde and melamine/formaldehyde resins;

alkyd resins
including glycerol-phthalic acid resins and mixtures thereof with melamine/formaldehyde resins; and unsaturated polyester resins
derived from copolyesters of saturated and unsaturated dicarboxylic acids with polyhydric alcohols as well as from vinyl compounds as cross-linking agents, and also halogenated flame-resistant modifications thereof.

The amount of the stabilizers of the invention needed for effective stabilization of polymers will depend on a variety of factors, such as the type and property of the polymers concerned, its intended use, and the presence of other stabilizers. It is generally satisfactory to use from 0.01 to 5.0% by weight of the stabilizers of the invention based on the weight of the polymer, but the most effective range will vary with the type of polymer: viz. 0.01 to 2.0%, preferably 0.02 to 1.0%, by weight for olefin, diene and styrene polymers; 0.01 to 1.0%, preferably 0.02 to 0.5%, by weight for vinyl chloride and vinylidene chloride polymers; and 0.01 to 5.0%, preferably 0.02 to 2.0%, by weight for polyurethanes and polyamides. If desired, two or more of the stabilizers of the invention may be used together.

The stabilizers of the invention may readily be incorporated into polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric composition of the invention may optionally contain various additives conventionally used in polymer technology, such as the additives listed in British Patent specification No. 1 401 924, at pages 11–13.

The invention is further illustrated by the following Examples, in which all parts and percentages are by weight.

EXAMPLE 1

N,N-Bis[2-hydroxy-3-(7,7,8,9,9-pentamethyl-2,4-dioxo-1,3,8-triazaspiro[4.5]dec-3-yl)propyl]decylamine (Compound No. b-11)

To a solution of 3.0 g of 7,7,8,9,9-pentamethyl-3-(2,3-epoxypropyl)-2,4-dioxo-1,3,8-triazaspiro[4.5]decane and 0.8 g of decylamine in 100 ml of methanol was added 0.1 g of potassium hydroxide, and the mixture was heated under reflux for 8 hours. After completion of the reaction, the mixture was condensed to a volume of 50 ml and allowed to stand at room temperature. The crystals precipitated were collected by filtration, washed with a small amount of methanol, dried under reduced pressure, and recrystallized from benzene to afford the desired compound as white crystals of m.p. 180° C.

EXAMPLE 2

N,N-Bis[2-hydroxy-3-(7,7,8,9,9-pentamethyl-2,4-dioxo-1,3,8-triazaspiro[4.5]dec-3-yl)propyl]butylamine (Compound No. b-7)

Using 3.0 g of 7,7,8,9,9-pentamethyl-3-(2,3-epoxypropyl)-2,4-dioxo-1,3,8-triazaspiro[4.5]decane and 0.36 g of butylamine, the reaction and the post-treatment were carried out according to the same procedures as in Example 1. The crude crystals thus obtained were recrystallized from toluene to afford the desired compound as white crystals of m.p. 178° C.

EXAMPLE 3

N-(2,2,6,6-Tetramethyl-4-piperidyl)-N-[2-hydroxy-3-(7,7,8,9,9-pentamethyl-2,4-dioxo-1,3,8-triazaspiro[4.5]-dec-3-yl)propyl]butylamine (Compound No. d-4)

Using 3.0 g of 7,7,8,9,9-pentamethyl-3-(2,3-epoxypropyl)-2,4-dioxo-1,3,8-triazaspiro[4.5]decane and 2.1 g of 2,2,6,6-tetramethyl-4-butylaminopiperidine, the reaction and the post-treatment were carried out according to the same procedures as in Example 1. The crude crystals thus obtained were recrystallized from benzene to afford the desired compound as white crystals of m.p. 74°–76° C.

EXAMPLE 4

3-[3-Di(2-hydroxyethyl)amino-2-hydroxypropyl]-7,7,8,9,9-pentamethyl-2,4-dioxo-1,3,8-triazaspiro[4.5]-decane (Compound No. c-11)

Using 3.0 g of 7,7,8,9,9-pentamethyl-3-(2,3-epoxypropyl)-2,4-dioxo-1,3,8-triazaspiro[4.5]decane and 1.1 g of diethanolamine, the reaction and the post-treatment were carried out according to the same procedures as in Example 1. The crude crystals thus obtained were recrystallized from benzene to afford the desired compound as white crystals of m.p. 155°–156° C.

EXAMPLE 5

N,N,N',N'-Tetra[2-hydroxy-3-(7,7,8,9,9-pentamethyl-2,4-dioxo-1,3,8-triazaspiro[4.5dec-3-yl)propyl]-hexamethylenediamine (Compound No. f-3)

Using 3.0 g of 7,7,8,9,9-pentamethyl-3-(2,3-epoxypropyl)-2,4-dioxo-1,3,8-triazaspiro[4.5]decane and 0.25 g of hexamethylenediamine, the reaction and the post-treatment were carried out according to the same procedures as in Example 1. The crude crystals thus obtained were recrystallized from ethanol to afford the desired compound as white crystals of m.p. 274°–275° C.

EXAMPLE 6

N,N,N',N'-Tetra[2-hydroxy-3-(7,7,8,9,9-pentamethyl-2,4-dioxo-1,3,8-triazaspiro[4.5]dec-3-yl)propyl]-p-xylenediamine (Compound No. f-6)

Using 3.0 g of 7,7,8,9,9-pentamethyl-3-(2,3-epoxypropyl)-2,4-dioxo-1,3,8-triazaspiro[4.5]decane and 0.3 g of p-xylenediamine, the reaction and the post-treatment were carried out according to the same procedures as in Example 1. The crude crystals thus obtained were recrystallized from benzene to afford the desired compound as white crystals of m.p. 128°–131° C.

EXAMPLE 7

3-(3-Diethylamino-2-hydroxypropyl)-7,7,8,9,9-pentamethyl-2,4-dioxo-1,3,8-triazaspiro[4.5]decane (Compound No. c-1)

Using 3.0 g of 7,7,8,9,9-pentamethyl-3-(2,3-epoxypropyl)-2,4-dioxo-1,3,8-triazaspiro[4.5]decane and 0.7 g of diethylamine, the reaction was carried out according to the same procedures as in Example 1. After completion of the reaction, methanol was removed by distillation and the residue was dissolved in ethyl acetate. The solution was washed with water, dried over sodium sulfate, and ethyl acetate was evaporated to give crude crystals, which were recrystallized from ethyl acetate to give the desired compound as white crystals of m.p. 140°–143° C.

EXAMPLE 8

3-(3-Cyclohexylamino-2-hydroxypropyl)-7,7,8,9,9-pentamethyl-2,4-dioxo-1,3,8-triazaspiro[4.5]decane (Compound No. a-21)

To a solution of 3.0 g of 7,7,8,9,9-pentamethyl-3-(2,3-epoxypropyl)-2,4-dioxo-1,3,8-triazaspiro[4.5]decane and 1.0 g of cyclohexylamine in 100 ml of methanol was added 0.1 g of potassium hydroxide, and the mixture was heated under reflux for 18 hours. After completion of the reaction, the mixture was filtered and the solvent was evaporated from the filtrate. The residue was dissolved in ethyl acetate, the solution washed with water, dried over sodium sulfate, and the solvent was removed by distillation. The crude crystals thus obtained were purified through a silica gel column chromatography using a mixture of ethyl acetate and methanol (2:1) as the first eluent and methanol as the second eluent to afford the desired compound as white crystals of m.p. 159°–163° C.

EXAMPLE 9

N,N-Bis[2-hydroxy-3-(7,7,8,9,9-pentamethyl-2,4-dioxo-1,3,8-triazaspiro[4.5]dec-3-yl)propyl]benzylamine (Compound No. b-31)

To a solution of 5.9 g of 7,7,8,9,9-pentamethyl-3-(2,3-epoxypropyl)-2,4-dioxo-1,3,8-triazaspiro[4.5]decane and 1.1 g of benzylamine in 100 ml of methanol was added 0.1 g of potassium hydroxide, and the mixture was heated under reflux for 12 hours. After completion of the reaction, the mixture was treated according to the same procedures as in Example 8 and the crude crystals thus obtained were purified through a silica gel column chromatography using a mixture of benzene and ethyl acetate (1:1) as the first eluent and a mixture of ethyl acetate and methanol (1:1) as the second eluent to afford the desired compound as white crystals of m.p. 86°–96° C.

EXAMPLE 10

N,N,N′,N′-Tetra[2-hydroxy-3-(7,7,8,9,9-pentamethyl-2,4-dioxo-1,3,8-triazaspiro[4.5]dec-3-yl)propyl]-2,4-diamino-6-phenyl-1,3,5-triazine (Compound No. f-13)

A mixture of 3.0 g of 7,7,8,9,9-pentamethyl-3-(2,3-epoxypropyl)-2,4-dioxo-1,3,8-triazaspiro[4.5]decane and 0.44 g of benzoguanamine was heated at 170°–180° C. for 4 hours. After completion of the reaction, the mixture was crystallized from benzene to afford the desired compound as pale yellow crystals of m.p. 145°–154° C.

EXAMPLE 11

N,N-Bis[2-hydroxy-3-(7,7,8,9,9-pentamethyl-2,4-dioxo-1,3,8-triazaspiro[4.5]dec-3-yl)propyl]cyclohexylamine (Compound No. b-26)

A mixture of 5.9 g of 7,7,8,9,9-pentamethyl-3-(2,3-epoxypropyl)-2,4-dioxo-1,3,8-triazaspiro[4.5]decane and 1.0 g of cyclohexylamine was heated at 140° C. for 30 minutes. After completion of the reaction, the mixture was dissolved in hot dichloroethane, the solution filtered, and the solvent was evaporated from the filtrate to give crude crystals, which were washed with ethyl acetate and dried under reduced pressure to afford the desired compound as white crystals of m.p. 230°–235° C.

EXAMPLE 12

N,N-Bis[2-hydroxy-3-(7,7,8,9,9-pentamethyl-2,4-dioxo-1,3,8-triazaspiro[4.5]dec-3-yl)propyl]octadecylamine (Compound No. b-20)

A mixture of 5.9 g of 7,7,8,9,9-pentamethyl-3-(2,3-epoxypropyl)-2,4-dioxo-1,3,8-triazaspiro[4.5]decane and 2.7 g of octadecylamine was heated at 180° C. for 24 hours. After completion of the reaction, the mixture was crystallized from ethyl acetate to afford the desired compound as white crystals of m.p. 166°–171° C.

EXAMPLE 13

N,N-Bis[2-hydroxy-3-(7,7,9,9-tetramethyl-2,4-dioxo-1,3,8-triazaspiro[4.5]dec-3-yl)propyl]octadecylamine (Compound No. b-19)

Using 1.2 g of 7,7,9,9-tetramethyl-3-(2,3-epoxypropyl)-2,4-dioxo-1,3,8-triazaspiro[4.5]decane and 0.54 g of octadecylamine, the reaction and the post-treatment were carried out according to the same procedure as in Example 9 to afford the desired compound as white crystals of m.p. 56°–58° C.

EXAMPLE 14

N,N-Bis[2-hydroxy-3-(7,7,9,9-tetramethyl-2,4-dioxo-1,3,8-triazaspiro[4.5]dec-3-yl)propyl]benzylamine (Compound No. b-30)

To a solution of 1.4 g of 7,7,9,9-tetramethyl-3-(2,3-epoxypropyl)-2,4-dioxo-1,3,8-triazaspiro[4.5]decane and 0.27 g of benzylamine in 10 ml of methanol was added 0.05 g of potassium hydroxide, and the mixture was heated under reflux for 9 hours. After completion of the reaction, the solvent was removed by distillation from the reaction mixture and the residue was dissolved in chloroform. The solution was washed with water, dried over sodium sulfate, the solvent was evaporated under reduced pressure to afford the desired compound as white crystals of m.p. 180°–185° C.

EXAMPLE 15

3-[3-Di{2-(4-tert-butylbenzoyloxy)ethyl}amino-2-{4-tert-butylbenzoyloxy}propyl]-7,7,8,9,9-pentamethyl-2,4-dioxo-1,3,8-triazaspiro[4.5]decane (Compound No. c-16)

In 250 ml of xylene were dissolved 2.9 g of 3-[3-di(2-hydroxyethyl)amino-2-hydroxypropyl]-7,7,8,9,9-pentamethyl-2,4-dioxo-1,3,8-triazaspiro[4.5]decane prepared in Example 4 and 6.0 g of methyl 4-tert-butylbenzoate, and 0.5 g of lithium amide was added to the solution. The mixture was heated under reflux for 8 hours and methanol formed was removed by distillation little by little together with xylene, while keeping the volume of the reaction mixture constant by adding xylene in an amount to conpensate the volume of the distilled methanol and xylene. After completion of the reaction, the mixture was washed with water, dried over sodium sulfate, and the solvent was evaporated to give crude crystals which were recrystallized from n-hexane to afford the desired compound as white crystals of m.p. 180°–181° C.

EXAMPLE 16

3-[3-Di{2-(3-(3,5-di-tert-butyl-4-hydroxyphenyl)propionyloxy)ethyl}amino-2-hydroxypropyl]-7,7,8,9,9-pentamethyl-2,4-dioxo-1,3,8-triazaspiro[4.5]decane (Compound No. c-17)

Using 2.0 g of 3-[3-di(2-hydroxyethyl)amino-2-hydroxypropyl]-7,7,8,9,9-pentamethyl-2,4-dioxo-1,3,8-triazaspiro-[4.5]decane prepared in Example 4 and 3.0 g of methyl 3-(3,5-di-tert-butyl-4-hydroxyphenyl)propionate, the reaction and the post-treatment were carried out according to the same procedures as in Example 15 to give a viscous oily substance, which was purified through a silica gel column chromatography using ethyl acetate as the eluent to afford the desired compound as a pale yellow viscous oily substance. The compound exhibited the Rf value of 0.55 in the silica gel thin layer chromatography using ethyl acetate as the developing solvent.

EXAMPLE 17

3-[3-Di(2-lauroyloxyethyl)amino-2-lauroyloxypropyl]-7,7,8,9,9-pentamethyl-2,4-dioxo-1,3,8-triazaspiro-[4.5]decane (Compound No. c-13)

Using 3.0 g of 3-[3-di(2-hydroxyethyl)amino-2-hydroxypropyl]-7,7,8,9,9-pentamethyl-2,4-dioxo-1,3,8-triazaspiro-[4.5]decane prepared in Example 4 and 4.9 g of methyl laurate, the reaction and the post-treatment were carried out according to the same procedures as in Example 16 to afford the desired compound as a colorless viscous oily substance. The compound showed the Rf value of 0.50 in a silica gel thin layer chromatography using ethyl acetate as the developing solvent.

EXAMPLE 18

N,N,N',N'-Tetra[2-acetoxy-3-(7,7,8,9,9-pentamethyl-2,4-dioxo-1,3,8-triazaspiro[4.5]dec-3-yl)propyl]-2,4-diamino-6-phenyl-1,3,5-triazine (Compound No. f-14)

A solution of 2.0 g of N,N,N',N'-tetra[2-hydroxy-3-(7,7,8,9,9-pentamethyl-2,4-dioxo-1,3,8-triazaspiro[4.5]-dec-3-yl)propyl]-2,4-diamino-6-phenyl-1,3,5-triazine prepared in Example 10 in 50 ml of acetic anhydride was heated at 100° C. for 5 hours. After completion of the reaction, acetic acid and acetic anhydride remained unreacted were removed by distillation from the reaction mixture. After addition of benzene to the residue, the mixture was washed with an aqueous 3% sodium carbonate solution and water, successively, dried over magnesium sulfate, and the solvent was evaporated to give crude crystals. Recrystallization of the crude crystals from benzene afforded the desired compound as pale yellow crystals of m.p. 166°–174° C.

EXAMPLE 19

3-(2-Hydroxy-3-tert-butylaminopropyl)-7,7,8,9,9-pentamethyl-2,4-dioxo-1,3,8-triazaspiro[4.5]decane (Compound No. a-6)

In a mixture of 15 ml of tetrahydrofuran and 20 ml of dimethylformamide were dissolved 10 g of 7,7,8,9,9-pentamethyl-3-(2,3-epoxypropyl)-2,4-dioxo-1,3,8-triazaspiro[4.5]-decane and 2.5 g of tert-butylamine and the solution was heated under reflux for 16 hours. After completion of the reaction, the mixture was poured into 25 ml of water, crystals precipitated were collected by filtration, washed with water and dried by heating under reduced pressure. The crude crystals thus obtained were recrystallized from ethyl acetate to afford the desired compound as white crystals of m.p. 177.0°–177.5° C.

EXAMPLE 20

N,N-Bis[2-hydroxy-3-(7,7,8,9,9-pentamethyl-2,4-dioxo-1,3,8-triazaspiro[4.5]dec-3-yl)propyl]dodecylamine (Compound No. b-13)

6.0 g of 7,7,8,9,9-pentamethyl-3-(2,3-epoxypropyl)-2,4-dioxo-1,3,8-triazaspiro[4.5]decane and 1.8 g of dodecylamine were reacted and treated according to the similar procedures as in Example 1, giving crude crystals. The crystals were recrystallized from a 5:1 by volume mixture of petroleum benzine and benzene, affording the desired compound in the form of white crystals melting at 186°–187° C.

EXAMPLE 21

3-(2-Hydroxy-3-dodecylaminopropyl)-7,7,8,9,9-pentamethyl-2,4-dioxo-1,3,8-triazaspiro[4.5]decane (Compound No. a-12)

29.5 g of 7,7,8,9,9-pentamethyl-3-(2,3-epoxypropyl)-2,4-dioxo-1,3,8-triazaspiro[4.5]decane and 9.0 g of dodecylamine were reacted and treated according to the similar procedures as in Example 1, giving crude crystals. The crystals were purified first by column chromatography through silica gel (eluent; ethyl acetate:benzene:ethanol:triethylamine=20:4:2:1), then by recrystallization from n-hexane, affording the desired compound in the form of white crystals melting at 88°–91° C.

EXAMPLE 22

N,N-Bis[2-hydroxy-3-(7,7,8,9,9-pentamethyl-2,4-dioxo-1,3,8-triazaspiro[4.5]dec-3-yl)propyl]octylamine (Compound No. b-9)

29.5 g of 7,7,8,9,9-pentamethyl-3-(2,3-epoxypropyl)-2,4-dioxo-1,3,8-triazaspiro[4.5]decane and 6.8 g of octylamine were reacted and treated according to the similar procedures as in Example 1, giving crude crystals. The crystals were recrystallized from ethanol, affording the desired compound in the form of white crystals melting at 188°–190° C.

EXAMPLE 23

N,N-Bis[2-hydroxy-3-(7,7,9,9-tetramethyl-2,4-dioxo-1,3,8-triazaspiro[4.5]dec-3-yl)propyl]dodecylamine (Compound No. b-12)

A mixture of 3.7 g of 7,7,9,9-tetramethyl-3-(2,3-epoxypropyl)-2,4-dioxo-1,3,8-triazaspiro[4.5]decane, 1.2 g of dodecylamine and 10 ml of octanol was heated at 100° C. for 5 hours, under stirring. After completion of the reaction, the octanol was evaporated by distillation under reduced pressure. The resulting residue was purified by column chromatography through silica gel (eluent; benzene:ethyl acetate:triethylamine:ethanol = 12:12:3:1), dissolved in benzene. By adding a 1:1 by volume mixture of ethyl acetate and n-hexane, there was obtained the desired compound in the form of white crystals melting at 85°–115° C.

EXAMPLE 24

A mixture of 100 parts of non-stabilized polypropylene powder (MFI-18), 0.2 part of stearyl 3-(3,5-di-tert-butyl-4-hydroxyphenyl)propionate and 0.25 part of a stabilizer of the present invention was kneaded homogeneously at 200° C. for 10 minutes by means of Brabender plastograph. The mass thus formed was compress-molded into a sheet of 2–3 mm thick using a laboratory press. The sheet was then pressed at the pressure of 12 tons by a hydraulic press under heating at 260° C. for 6 minutes, and then immediately poured into cold water to form a film of 0.5 mm thick, from which a film of 0.1 mm thick was prepared by a similar manner and cut into test pieces of a size of 50×120 mm.

The test pieces were exposed to the light at a black-pannel temperature of 63°±3° C. in Sunshine-Weather Meter and each of the test pieces was periodically examined to determine the percentage of elongation at break. Results of the tests were expressed by the ratio of the time until the elongation rate at break of the test pieces reached 50% of that at 0 hour of the test, and the time determined by the same way for the control pieces which were irradiated without adding the stabilizer of the invention, as shown in Table 1.

Table I

| Compound No. | Ratio | Compound No. | Ratio |
| --- | --- | --- | --- |
| a- 12 | 6.8 | b- 30 | 5.1 |
| 21 | 7.5 | 31 | 5.3 |
| b- 7 | 5.0 | c- 1 | 6.1 |
| 9 | 5.7 | 17 | 5.2 |
| 11 | 6.1 | d- 4 | 6.8 |
| 12 | 6.0 | f- 6 | 4.7 |
| 13 | 7.7 | 13 | 4.2 |
| 19 | 6.7 | 14 | 5.9 |
| 20 | 6.0 | | |

EXAMPLE 25

To 100 parts of non-stabilized polystyrene pellets (Trade name; Styrone 666, product of Asahi-Dow Co.) was added 0.25 part of a stabilizer of the invention and the mixture was kneaded homogeneously at 200° C. for 5 minutes by means of Brabender plastograph. The mass thus prepared was immediately pressed into a plate of 2–3 mm thick, which was further press-molded at 180° C. for 2 minutes into a plate of 1.5 mm thick. The plates were irradiated at a black pannel temperature of 63°±3° C. for 1500 hours in BH-type Xenon . Weather-O-Meter (65 WR-type; 6500 watt lamp of water-cooling type, supplied from Atlas Co.) according to the method C specified under the ASTM G26. The yellowness index was estimated according to the method of the ASTM D 1925 and results obtained are shown in Table 2.

Table 2

| Compound No. | $YI_O$ | $YI_{1500}$ |
| --- | --- | --- |
| a- 21 | 1.8 | 8.3 |
| b- 12 | 2.6 | 10.8 |
| 13 | 2.0 | 9.8 |
| 20 | 2.0 | 9.1 |
| 30 | 2.0 | 8.5 |
| 31 | 1.9 | 8.8 |
| c- 17 | 2.2 | 9.4 |
| d- 4 | 2.1 | 9.8 |
| f- 13 | 2.2 | 9.5 |
| No Addition | 1.8 | 36.5 |

EXAMPLE 26

In 300 parts of dimethylformamide were homogeneously dissolved 100 parts of thermoplastic polyurethane (Trade name; Paraprene Pellet 22S, product of Nippon Polyurethane Kogyo Co.) and 0.25 part of a stabilizer of the invention, and the solution was spread on a glass plate to make a layer of about 0.4 mm thick, dried at 60° C. for 20 minutes and then at 120° C. for 15 minutes to give a film of about 0.1 mm thick. The film was irradiated at a black pannel temperature of 63°±3° C. for 300 hours without the water spray in Sunshine . Carbon Arc-Weather-Meter. The yellowness index was estimated according to the method of the ASTM D 1925, and results obtained are shown in Table 3.

Table 3

| Compound No. | $YI_O$ | $YI_{300}$ |
| --- | --- | --- |
| b- 12 | 1.8 | 21.3 |
| 13 | 1.6 | 21.3 |
| 20 | 2.2 | 23.8 |
| 30 | 2.1 | 23.0 |
| 31 | 1.9 | 25.1 |
| d- 4 | 2.0 | 21.3 |
| f- 13 | 2.0 | 23.6 |
| No Addition | 1.5 | 48.0 |

What is claimed is:

1. A piperidine-spiro-hydantoin derivative having the formula

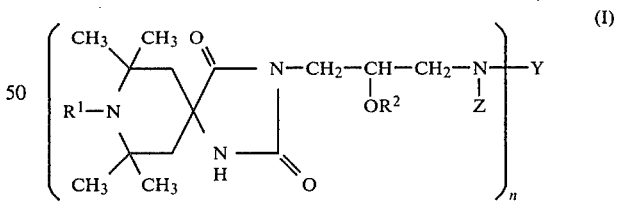

and an acid addition salt thereof wherein $R^1$ represents hydrogen or methyl, $R^2$ represents hydrogen or an acyl group having not more than 18 C-atoms, n is 1 or 2, when n is 1, Y and Z may be the same or different and represent hydrogen, and alkyl group having from 1–18 C-atoms, an alkenyl group having from 3–18 C-atoms, a cycloalkyl group having from 5–7 C-atoms, a phenyl group optionally substituted with methyl, an aralkyl group having 7 or 8 carbon atoms, a group of the formula

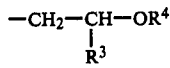

(II)

(wherein R³ represents hydrogen or methyl and R⁴ represents hydrogen or an acyl group having not more than 18 carbon atoms;)
2,2,6,6-tetramethyl-4-piperidyl or 1,2,2,6,6-pentamethyl-4-piperidyl or a group of the formula

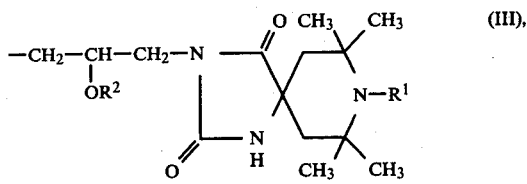

(III), or Y and Z may be joined together to form a tetramethylene, pentamethylene, 3-oxapentamethylene, succinyl, glutaryl, maleoyl or phthaloyl group or a group of the formula

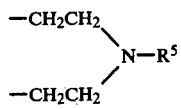

wherein R⁵ is a group of the formula (III), with the proviso that R² and R⁴ are hydrogen when Y and/or Z are hydrogen and that R² and R⁴ are each hydrogen or an acyl group as defined or R² is hydrogen and R⁴ is an acyl group as defined when Y and Z are both a group of the formula (II) or one of Y and Z is a group of the formula (II) and the other is different from hydrogen; when n is 2, Y represents an alkylene group having from 2–6 carbon atoms, a phenylene group which may be substituted by methyl, p-xylylene, 1,4-cyclohexylene, the 4,4'-diphenylether or 4,4'-diphenylmethane radical, 2,4-s-triazinediyl, 6-methyl- or 6-phenyl-2,4-s-triazinediyl, and Z represents a group of the formula (III), 2,2,6,6-tetramethyl-4-piperidyl or 1,2,2,6,6-pentamethyl-4-piperidyl.

2. A compound as claimed in claim 1 wherein, when n is 1, Y and Z are the same or different and represent hydrogen, alkyl having from 1–18 carbon stoms, alkenyl having from 3–18 carbon atoms, cycloalkyl having from 5–7 carbon atoms, aralkyl having 7 or 8 carbon atoms, a group of the formula (II) or a group of the formula (III) with the proviso that, when Y and Z both represent alkyl, alkenyl, cycloalkyl, aralkyl or a group of the formula (II) as defined, said groups are identical, and when n is 2, Y represents alkylene having from 2–6 carbon atoms, p-xylylene, 2,4-s-triazinediyl, 6-methyl- or 6-phenyl-2,4-s-triazinediyl, and Z represents a group of the formula (III).

3. A compound as claimed in claim 2 wherein R² is hydrogen.

4. A compound as claimed in claim 2 wherein n is 1, R² is hydrogen, Y represents alkyl having from 1–18 carbon atoms, cyclohexyl or benzyl and Z represents hydrogen or a group of the formula (III) wherein R² is hydrogen.

5. A compound as claimed in claim 4 wherein Z is a group of the formula (III), and n, Y and R² have the same meaning as in claim 4.

6. A compound as claimed in claim 4 wherein Y represents alkyl having from 8–18 carbon atoms, Z represents a group of the formula (III) and n and R² are as defined in claim 4.

7. A compound as claimed in claim 2 wherein n is 2, Y represents alkylene having from 2–6 carbon atoms, p-xylylene or 6-phenyl-2,4-s-triazinediyl, Z is a group of the formula (III) and R² is hydrogen.

8. A compound as claimed in claim 2 wherein R² and R⁴ are the same or different and represent alkanoyl having not more than 18 carbon atoms, 3-(3,5-di-tert-butyl-4-hydroxyphenyl)propionyl or benzoyl which may be substituted by an alkyl group having from 1–4 carbon atoms.

9. A compound as claimed in claim 1 wherein R² is hydrogen, Z represents a 2,2,6,6-tetramethyl-4-piperidyl or 1,2,2,6,6-pentamethyl-4-piperidyl group, n is 1 or 2, and Y, when n is 1, represents alkyl having from 1–18 carbon atoms and, when n is 2, Y represents alkylene having from 2–6 carbon atoms.

10. A composition comprising a synthetic polymer and a piperidine-spiro-hydantoin derivative of the formula (I) or an acid addition salt as claimed in claim 1 as stabilizer.

11. A synthetic polymer composition as claimed in claim 10 wherein the polymer is an olefin or diene polymer, a styrene polymer or polyurethane.

* * * * *